United States Patent [19]

Schindler et al.

[11] Patent Number: 5,782,913
[45] Date of Patent: Jul. 21, 1998

[54] SOFT TISSUE AUGMENTATION APPARATUS

[75] Inventors: Robert Schindler, San Francisco; Corey Maas, Sausalito, both of Calif.

[73] Assignee: The Regents of the University of California, Oakland, Calif.

[21] Appl. No.: 677,635

[22] Filed: Jul. 8, 1996

Related U.S. Application Data

[62] Division of Ser. No. 379,007, Jan. 27, 1995, Pat. No. 5,607,477, which is a continuation of Ser. No. 90,518, Jul. 12, 1993, abandoned.

[51] Int. Cl.$^6$ .................................................. A61F 2/02
[52] U.S. Cl. .......................................... 623/11; 623/10
[58] Field of Search ........................... 206/439; 623/12, 623/10, 11

[56] References Cited

U.S. PATENT DOCUMENTS

| | | | |
|---|---|---|---|
| 3,547,257 | 12/1970 | Armentrout | 206/439 |
| 4,306,318 | 12/1981 | Mano et al. | |
| 4,421,235 | 12/1983 | Moriya | 206/439 X |
| 4,550,831 | 11/1985 | Whitford | 206/439 |
| 4,662,885 | 5/1987 | DiPisa, Jr. | |
| 4,838,280 | 6/1989 | Haaga | |
| 4,854,316 | 8/1989 | Davis | |
| 4,936,835 | 6/1990 | Haaga | |
| 4,963,150 | 10/1990 | Brauman | |
| 5,007,926 | 4/1991 | Derbyshire | |
| 5,024,671 | 6/1991 | Tu et al. | |
| 5,147,374 | 9/1992 | Fernandez | |
| 5,147,387 | 9/1992 | Jansen et al. | |
| 5,236,447 | 8/1993 | Kubo et al. | |
| 5,246,452 | 9/1993 | Sinnott | |
| 5,263,969 | 11/1993 | Phillips | |
| 5,304,187 | 4/1994 | Green et al. | |
| 5,405,379 | 4/1995 | Lane | |
| 5,573,544 | 11/1996 | Simon et al. | 606/151 |

FOREIGN PATENT DOCUMENTS

| | | |
|---|---|---|
| 262365A1 | 11/1988 | Germany |
| 92/10218 | 6/1992 | WIPO |
| 93/05730 | 4/1993 | WIPO |

OTHER PUBLICATIONS

Photocopies of front and back side of a "Vascular Graft" package of Atrium Medical Corporation.

Beekhuis, "Mersilene Mesh to Augment the Nasal Bridge," *Am. J. Cosmetic Surgery*, 3:2. pp. 49–53 (1986).

Maas et al., "Comparison of Biomaterials for Facial Bone Augmentation," *Arch Otolaryngol Head Neck Surg, 116*. pp. 551–556 (1990).

Mole, "The Use of Gore–Tex Implants in Aesthetic Surgery of the Face," *Plastic and Reconstructive Surgery, 90*:2. pp. 200–206 (1992).

Mole, "Intérêt des Implants Protétiques Souples Dans la Chirurgie du Rajeunissement Facial," *Annales de Chirurgie Plastique et Esthétique, 34*:3. pp. 227–233 (1989).

Mole, "Interest of Supple Prosthetic Implants in Facial Rejuvenation Surgery," English translation of the French article identified above as reference C4.

Rothstein et al., "The Use of Gore–Tex Implants in Nasal Augmentation Operations," *ENTechnology*. pp. 40–45 (1989).

Schoenrock et al., "Gore–Tex in Facial Plastic Surgery," *Intern. J. of Aesthetic & Restorative Surgery, 1*:1. pp. 63–68 (1993).

(List continued on next page.)

*Primary Examiner*—David H. Willse
*Attorney, Agent, or Firm*—Majestic, Parsons, Siebert & Hsue

[57] ABSTRACT

A soft tissue augmentation kit comprises a flexible implant and an insertion tool for the implant. The implant is formed of a biocompatible material that is permeable to red blood cells and includes a cavity. The cavity opens to the exterior and permits fibrous tissue ingrowth. The insertion tool carries the implant via the cavity for insertion into selected soft tissue. When the insertion tool is removed the implant is left in the selected tissue.

6 Claims, 2 Drawing Sheets

OTHER PUBLICATIONS

Stucker et al., "Technical Aspects of Facial Contouring Using Polyamide Mesh," *Otolaryngologic Clinics of North America*, 15:1, pp. 123–131 (1982).

Stucker, "Use of Implantation in Facial Deformities," *Laryngoscope*, 87, pp. 1523–1527 (1977).

Waldman, "Gore–Tex for Augmentation of the Nasal Dorsum: A Preliminary Report," *Ann. Plast. Surg.*, 26, pp. 520–525 (1991).

Maas et al., "Expanded Polytetrafluoroethylene (Gore–Tex) in Facial Augmentation," presented Jan. 19, 1992 before the Am. Acad. Facial Plast & Recons Surg, accpt. for pub in *Arch of Otolaryn–Head & Neck Surg*, (1993).

Glasgold et al., "Gore–Tex Soft–Tissue Implants," *Applications of Biomaterials in Facial Plastic Surgery*, CRC Press, pp. 328–334 (date unknown).

Ellis et al., "Labial Commissure Groove Augmentation Using Gore–Tex," abstract from the 6th International Symposium of Facial Plastic Surgery (1993).

Reppucci et al., "Critical Review of Clinical Experience with Gore–Tex in Facial Contouring," abstract from the 6th International Symposium of Facial Plastic Surgery (1993).

Product Information literature describing "New Beginnings" dermal transfer cannula set of PMT Corporation (1992).

Front and Back of "Gore–Tex Soft Tissue Patch 2 mm" Product Packaging, W.L. Gore & Associates, Inc.

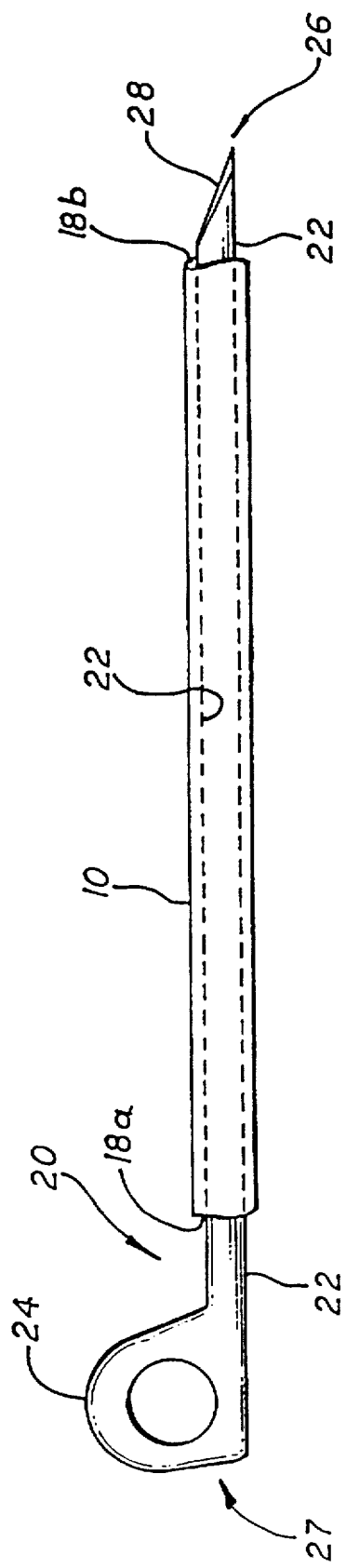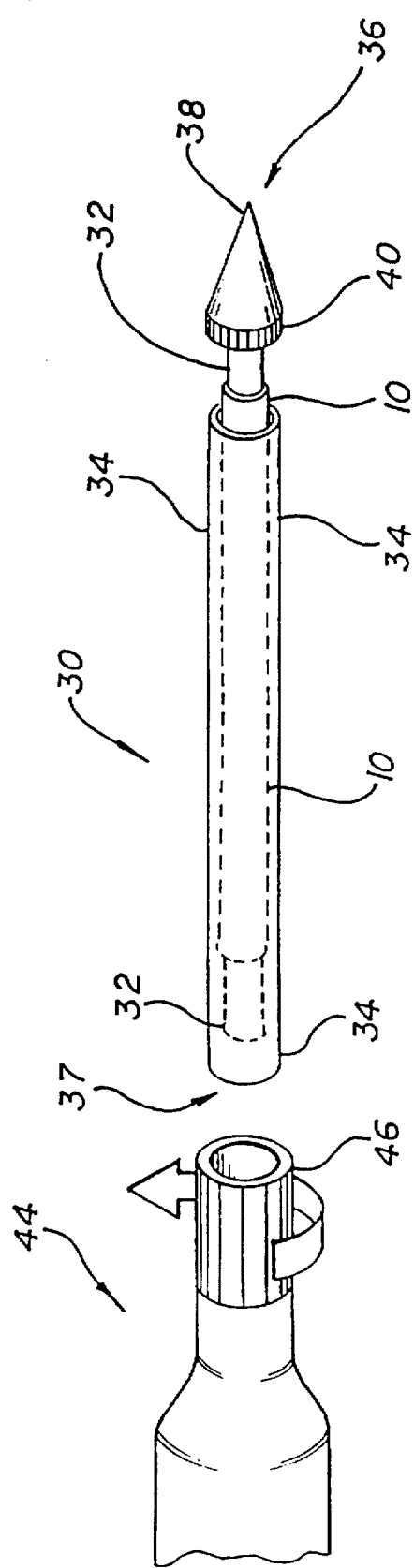

SOFT TISSUE AUGMENTATION APPARATUS

This is a division of U.S. application Ser. No. 08/379,007, filed Jan. 27, 1995, now U.S. Pat. No. 5,607,477, which is a continuation of application Ser. No. 08/090,518, filed Jul. 12, 1993, now abandoned.

FIELD OF THE INVENTION

This invention relates generally to soft tissue augmentation, and more particularly to corrections of soft tissue defects by the insertion of biocompatible flexible implants having a cavity into which fibrous tissue can grow and thus which predictably and stably augment tissue defects.

BACKGROUND OF THE INVENTION

Soft tissue augmentation can be temporary or permanent. Temporary corrections can be achieved by lifting (e.g. face lifting), fat or collagen injections. Permanent corrections have been suggested through the use of homogenic and alloplastic implants. Homogeneous implants can have absorption problems and further incur disease transmission problems.

The properties of various synthetic implant materials have been reported when used in facial augmentation procedures, particularly for reconstructions. Synthetic implants have been used in augmentation procedures. The materials used include solid, medical-grade silicone rubber ("Silastic," available from Dow-Corning Corp., Midland, Mich.), braided, multifilament PET ("Mersilene," available from Ethicon Corp., Summerville, N.J.), polyamide mesh ("Supramid," available from S. Jackson, Inc., Alexandria, Va.), polytetrafluoroethylene resin ("Teflon," available from C. R. Baird, Inc., Billerica, Mass.), polytetrafluoroethylene carbon ("Proplast," available from Vitek, Inc., Houston, Tex.), hydroxyapatite (available from Integrated Orbital Implants, San Diego, Calif.), and expanded, fibrillated polytetrafluoroethylene, or PTFE ("Gore-Tex," available from W. L. Gore, Phoenix, Ariz.).

Thus, Stucker reports firming rolling polyamide mesh and placing the implants in incised locations to correct nasal dorsal deformities, for chin augmentation, or for underdeveloped maxilla associated with cleft lip nose. Stucker, "Use of Implantation in Facial Deformities," *Laryngoscope*, 87, pp. 1523–1527 (1977). Later, Stucker and coauthors reported further facial contouring procedures, again using polyamide mesh, which was folded into layers and then tightly rolled. These implants were used to augment the nasal dorsum through incisions to prepare the recipient site. Stucker et al., "Technical Aspects of Facial Contouring Using Polyamide Mesh," *Otolaryngol. Clin. North Am.*, 15:1, pp. 123–131 (1982).

However, polyamide when implanted gives rise to some tissue reaction and undergoes some hydrolytic degradation that results in a gradual loss of tensile strength. Thus, Beekhuis describes use of Mersilene mesh as an alternative dorsal nasal filler in saddle nose deformities, for chin implants, and the like reconstructive surgical procedures. Beekhuis, "Mersilene Mesh to Augment the Nasal Bridge," *Am. J. Cosmetic Surg.*, 3:2 (1986).

Maas et al. compared the gross behavior of various currently used implant materials for facial bone augmentation at different sites in dogs. The authors concluded that the site of implantation and implant movement were important factors in determining the nature of the tissue response and the fate of implants. Maas et al., "Comparison of Biomaterials for Facial Bone Augmentation," *Arch. Otolaryngol. Head Neck Surg.*, 116, pp. 551–556 (1990).

Several authors have recently discussed the use of Gore-Tex implants. Thus, Rothstein et al. have used patches of the PTFE material for saddle nose deformities in nasal augmentation operations. Rothstein et al., "The Use of Gore-Tex Implants in Nasal Augmentation Operations," *EN Technology*, pp. 40–45, (1989). Similarly, Waldman reports use of Gore-Tex soft tissue patches as dorsal implants where the patch (or layers of patches) was placed over incisions and intranasal and extranasal incisions closed. Waldman, "Gore-Tex for Augmentation of the Nasal Dorsum: A Preliminary Report," *Anal. Plas. Surg.*, 26:6 (1991). Mole has used patches or strips of the material inserted by a needle-like instrument with the implant kept in place using a transfixing cutaneous needle. Mole, "The Use of Gore-Tex Implants in Aesthetic Surgery of the Face," *Plas. Reconst. Surg.*, 90:2, pp. 200–206 (1992).

However, the strips, patches, sandwiches, and tightly rolled forms of implants previously and presently used have had various drawbacks and disadvantages, such as the necessity for relatively large incisions to achieve implantation and the limited amount of tissue ingrowth.

SUMMARY OF THE INVENTION

In one aspect of the present invention, a soft tissue augmentation kit comprises a flexible implant and an insertion tool for the implant. The implant defines an interior cavity which can serve several functions. The cavity can permit the implant to be mounted or carried by the insertion tool, preferably so that the implant can be inserted and positioned subcutaneously into soft tissue through a very small incision. The cavity can also serve for anchoring the implant by fibrous tissue ingrowth.

The implant is formed of a biocompatible material, and preferably has a cross-section between exterior and interior surfaces that is permeable to red blood cells. Preferred permeability is where the cross section has pores of between about 10 to about 50μ.

Additional objects, advantages, and novel features of the invention will be set forth in the description which follows and will also become apparent to those skilled in the art.

BRIEF DESCRIPTION OF THE DRAWINGS

FIG. 2 is a side view of one kit embodiment of the invention; and

FIG. 3 is an exploded side view, partially broken away, of a second kit embodiment.

DETAILED DESCRIPTION OF THE PREFERRED EMBODIMENTS

Figure 1:
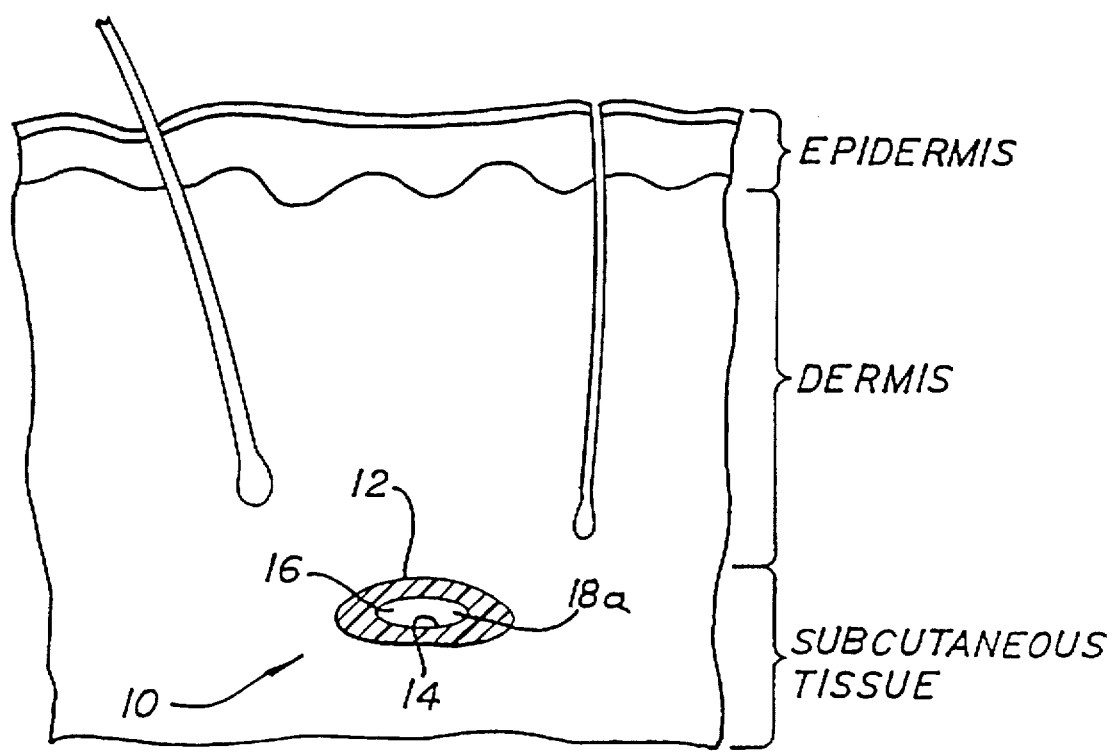
FIG. 1 is a cross-section, broken away, illustrating soft tissue from the outermost layer of the epidermis into the subcutaneous layer with an implanted embodiment of the invention in place.

Implants of the invention are flexible. When this flexibility is combined with an interior cavity, the implant after insertion in soft tissue will tend to assume a sloping, smoothly tapered shape. For example, with reference to FIG. 1, an implant 10 embodiment is illustrated having an exterior surface 12, and interior surface 14, and a cavity 16. The FIG. 1 illustration shows implant 10 with a generally oval cavity 16, the oval shape of which results after a generally longitudinally extending body of flexible, porous material with a bore therethrough is implanted into soft tissue, such as where implant 10 is inserted subcutaneously under a glabellar facial wrinkle or a nasal labial fold.

In the FIG. 1 illustration of the implant 10 embodiment, cavity 16 has at least one opening 18a adjacent to the exterior surface 12 through which fibrous tissue grows into the cavity. As will be further described hereinafter, cavity 16 also serves as a means by which implant 10 can be carried on or by an insertion tool and then left in the desired position when the insertion tool is removed.

In the one preferred embodiment, implant 10 longitudinally extends and the cavity 16 is a bore therein and therethrough that opens at both ends to the exterior. Thus, cavity or bore 16 is in fluid communication with the surrounding soft tissue when inserted, and substantial tissue ingrowth will occur a suitable period of time after insertion. At least a portion of the implant between the exterior surface and the cavity, (transverse to the longitudinal axis a spaced distance from one end), preferably a cross-section between exterior surface 12 and interior surface 14, is permeable to red blood cells. This red blood cell permeability further encourages tissue ingrowth from exterior surface 12 towards cavity 16 after insertion and also assists in promoting flow of fluids into cavity 16 for tissue ingrowth and resultant implant 10 anchoring.

Implant 10 is formed of a biocompatible material that can be either non-biodegradable (for permanent implants) or biodegradable (for temporary implants). Biodegradable materials may be preferred for forming implants of this invention in instances such as lip augmentation, where a temporary effect may be desired.

Suitable biodegradable materials include woven polymers such as the glycolide/lactide copolymers available from Ethicon ("Vicryl") and polyglycolides available from American Cyanamid ("Dexon"). Such materials, in yarn form, have been used as semi-absorbable or absorbable suture materials.

However, implant embodiments of the invention will more typically be formed from non-biodegradable materials so as to be used as relatively permanent implants for augmenting soft tissues of the face and body such as scars, wrinkles, or depressions. Additional applications contemplated include breast implants, particularly in the case of post-operative cosmetic surgery follow mastectomies. In an application such as a breast implant, the inventive implants may desirably be combined with another material to form a composite. For example, into at least a portion of cavity 16 can be inserted an envelope containing a relatively high viscosity fluid, such as saline solution or a biodegradable, non-toxic and inert oil (e.g., peanut oil). Further, all of part of the body of the implant can include, carry, or be impregnated with a therapeutically effective drug, such as an antibiotic to prevent infection or fibroblast growth factors.

As will be understood, for the various desired applications by which implants of the invention will be used, the shape and dimensions will be varied by criteria readily ascertainable by persons skilled in the art.

Particularly contemplated is where a plurality of differently dimensioned implants will be sterilely packaged with the dimensions adapted for particular soft tissue areas selected for augmentation. For example, a sterile package (with any of various known means to open or release and permitting opening by the surgeon or assisting personnel at the time of insertion) can desirably include a pair of implants for both nasal labial folds and one or more, typically smaller or shorter implants for filling one or more glabellar facial wrinkles.

The package in which the implant or plurality of implants are maintained in sterile condition until use can take a variety of forms known to the art. The packaging material itself can be bacteria and fluid or vapor impermeable, such as film, sheet, or tube, polyethylene, polypropylene, poly (vinylchloride), and poly(ethylene terephthalate), with seams, joints, and seals made by conventional techniques, such as, for example, heat sealing and adhesive bonding. Examples of heat sealing include sealing through use of heated rollers, sealing through use of heated bars, radio frequency sealing, and ultrasonic sealing. Peelable seals based on pressure sensitive adhesives may also be used.

It will be understood that the choice of packaging material will be at least in part dependant on the method of sterilization to which the package will be subjected (e.g. steam autoclaving, exposure to ionizing radiation, or exposure to oxidizing gases such peracetic acid vapor as discussed by U.S. Pat. No. 5,084,239, issued Jan. 28, 1992, and U.S. Pat. No. 5,115,166, issued May 19, 1992.

The package can also include a portion that is permeable to gas or vapor, but impermeable to bacteria. Such a gas or vapor permeable portion will typically be microporous with the volume average diameter of pores being in the range of from about 0.02 to about 0.5μ. Suitable microporous materials include spun bonded polyethylene, spun bonded polypropylene, microporous polyethylene, and microporous polypropylene, usually in the form of film or sheet. Paper can also be used as the permeable portion. The gas or vapor permeable portion will normally be configured so as to define at least one path for providing entry of sterilizing gas, where post-packaging sterilization is contemplated. For example, U.S. Pat. No. 4,937,115, issued Jun. 26, 1990, discloses a sterilizable or sterilized package for packaging medical items.

Suitable biocompatible, non-biodegradable materials include expanded, fibrillated polytetrafluoroethylene ("Gore-Tex"), polyethylene terephthalate ("Mersilene"), polyamide, and the like materials, so long as they are biocompatible and sterilizable, can be formed into the desired shape with an interior cavity and have a permeable fluid and red blood path between exterior and the cavity. Sufficient permeability is whereby the implant is permeable to red blood cells (which are of about 6–7μ in diameter), preferably a permeability so that pores are in a size range of about 10 to about 50μ. Even larger pore diameters are feasible, but the textural compatibility to soft tissue will begin to be lost.

The implants can be formed into the desired shapes and sizes (e.g. small diameter tubes for wrinkles, but larger, more globular shapes for applications such as breast implants) by various conventional manufacturing techniques, such as, for example, extrusion.

The expanded, fibrillated PTFE material is particularly preferred due to studies demonstrating acceptable biocompatibility in a long-term animal model. This material has an average pore size of 22μ; however, it does not appear to allow sufficient fibrous tissue ingrowth for good anchoring. This is illustrated by Comparative Example 1.

COMPARATIVE EXAMPLE 1

The experimental (non-inventive) implants consisted of patches of fibrillated, expanded PTFE with thicknesses of 2 mm. There were no orifices in the implants, and the patches were prepared from packaged sheet materials sold by W. L. Gore.

Nine pathogen-free male and female New Zealand white rabbits weighing 2–4 kg were used in the study. Care, handling, and surgical procedures were performed in accordance with the guidelines and standards set by the Institutional Review Board's Committee on Animal and Human Research. The animals were anesthetized with intravenous ketamine (40 mg/kg) and xylazine (7 mg/kg).

After the animals were shaved and prepared, the nasal dorsum was draped and a 1.0 cm anterior incision was made through the skin and subcutaneous tissues. A limited subcutaneous pocket was formed using the scissors technique over the nasal dorsum. Laminated 1×2 cm implants were cut and preoperatively sterilized according to instructions on the package insert. The implants were then placed directly over bone with the peritoneum elevated, and the wound was closed with interrupted 4–0 nylon sutures. The animals were carefully observed on a daily basis for signs of wound infection, seroma, or hematoma formation. Sutures were removed one week postoperatively. The animals were euthanized prior to necropsy by injection of intravenous Phenobarbital. At the time of necropsy, all implants were carefully palpated and graded for stability using manual manipulation.

The animals were equally divided into early (3 weeks), intermediate (6 months), and long-term (12 months) implant groups. Tissue specimens including skin, implant, and underlying bone were removed en bloc. A portion of the bloc was used as a fresh tissue specimen for fixation and preparation for scanning electron microscopy.

All implants remained freely mobile by palpation after a 3 week period of implantation. None of the implants were lost or extruded and there was no evidence of wound infection, hematoma, or seroma formation. In the intermediate group (6 months), two of the six remaining test animal implants demonstrated stability within soft tissue, with four implants freely mobile within the soft tissues. The long-term (12 months) test animal implants demonstrated stability within soft tissue.

Within the substance of the material, no tissue ingrowth was observed in the early group. Little or no fibrosis was seen in this group, neither within the material substance nor at its periphery. Routine light microscopy did not show material substance loss, degradation, or breakdown in the early study group. When studied under scanning electron microscopy, the early group specimens demonstrated a delicate, fibrous network of tissue directly adherent to the material substance. In addition, a small number of acute and chronic inflammatory cells were seen in association with the material. No evidence of breakdown or degradation of a material substance was observed.

The intermediate study group (6 months) demonstrated absence of acute inflammatory cells at the tissue-implant interface. Scattered and moderate numbers of chronic inflammatory cells were seen focally, with an occasional, rare, foreign body giant cell present. The central portions of the material, however, demonstrated no ingrowth of host tissue or cells. No significant thickening occurred and minimal fibrous tissue ingrowth was seen at the periphery of the material. No evidence of destruction, loss of integrity, or resorption of the material was observed in this group. Scanning electron microscopy of the intermediate (6 month) implant group demonstrated an increase in the delicate but adherent fibrous tissue network over the implant surface. A few chronic and acute inflammatory cells were present; however, changes in the material's structural integrity were not apparent. The delicate fibrous pseudocapsule described on routine microscopy was closely adherent to the material.

The long-term (12 month) implant group demonstrated very little change in tissue response or material substance from the intermediate group. A delicate fibrous tissue capsule was consistently present in the three remaining animals, but showed no evidence of thickening occasional chronic inflammatory cells and a moderate number of fibroblasts were observed growing into the periphery of the implant and only scant and focal foreign body giant cells were present. No evidence of underlying bone changes or changes to the material's integrity was observed. Scanning electron microscopic studies of the long-term implant group also showed very little change in tissue character from the intermediate group. A small increase in the organization of the thin fibrous capsule and a slight thickening of the delicate stormily components of the adherent fibrous tissue was present. There were, however, vocal areas that suggested some loss of the surface integrity of the material. These areas were scattered and focal without consistency in their relationship to the underlying bone or soft tissue. No chronic inflammatory cell reaction or evidence of material phagocytosis was present in the area surrounding these focal irregularities. These areas may represent simple mechanical damage to the implant material during handling.

Thus, although the PTFE material is porous, it does not allow much fibrous tissue ingrowth, and the small amount of fibrous tissue ingrowth that does occur is only sufficient to confer some limited stability of an implant in the form of a solid structure in soft tissues over time. This conclusion appears to contradict information said to originate with W. L. Gore (see Rothstein et al., supra, footnote 9). However, the Gore-Tex material itself appears to be a safe and reliable substance. We believe one advantage provided by the inventive implants 10 requiring the presence of a cavity 16 with at least one end 18a open to the exterior is the property of substantial tissue ingrowth leading to secure anchoring of the inventive implants. Thus, inventive implants 10 avoid or reduce the palpable rigidity or movement that is inherent in cord or sheet forms.

Although one aspect of this invention is a soft tissue augmentation device that can consist essentially only of the inventive implant or plurality of implants, a soft tissue kit is contemplated that includes an insertion tool for the implant. The insertion tools will be of a construction either to be sterilizable or more preferably, all or part of the insertion tools will be disposable. Two insertion tool embodiments will now be described.

Turning to FIG. 2, implant 10 is shown mounted on or carried by an insertion tool 20 in its pre-insertion configuration. The insertion tool 20 comprises a relatively flexible, non-compressible, longitudinally extending shaft 22 with a distal end 26 and a proximal end 27. Shaft 22 preferably mates with, or conforms to, orifice 16 of implant 10.

Distal end 26 is comprised of a tapered tip 28 sharp enough to pierce the surface of the dermal layer under which the implant 10 is to be subcutaneously placed. Proximal end 27 is comprised of a handle 24 (either separately formed and attached to shaft 22 or formed as a unitary body with shaft 22).

In an example of operation, the physician manipulates handle 24 to push tip 28 through the dermis at the proximal end of the area where implant 10 is to be placed, thereby creating a subcutaneous canal.

The instrument is designed for the surgeon to push the sharp point through the intact skin. However, an incision can be made initially if the surgeon so desires or when the size of the implant dictates.

In the embodiment of FIG. 2, it is preferred that the tip 28 is allowed to exit the dermis at the opposite end of the implant area to adjust and stabilize the implant, though the dermis need not be exited if the surgeon so desires. Flexible shaft 24 follows tip 28 into the dermis, thereby positioning implant 10 at the desired location within the subcutaneous canal. While stabilizing the implant distally the shaft can be removed with a gentle twisting motion.

The length of shaft 22 up to and including distal end 26 is then removed from the canal through the proximal end of the incision originally made thereby leaving implant 10 in the location and position desired.

The first embodiment insertion tool 20 can be made in whole or part of materials such as stainless steel, rigid plastic, or carbon fibers. This first embodiment is preferably disposable.

A second insertion tool embodiment is shown in FIG. 3. Implant 10 is shown carried by insertion tool 30 in its pre-insertion configuration. The insertion tool 30 comprises outer cannula 34 and a relatively flexible, non-compressible, longitudinally extending central shaft 32 with distal end 36 and proximal end 37.

Distal end 36 is comprised of a conical or otherwise tapered tip 38 sharp enough to pierce the surface of the dermal layer under which the implant 10 is to be subcutaneously placed. On the surface of tip 38 is flat surface 40, knurled or otherwise textured to facilitate grasping tip 38.

Central shaft 32 is joined with tip 38 (either separately formed and attached to shaft 32 or formed as a unitary body with shaft 32). Implant 10 is mounted on or carried by central shaft 32. Outer cannula 34 is positioned over both central shaft 32 and implant 10 with its distal end adjacent to tip 38 and the opposite end protruding proximally beyond proximal end 36 of shaft 32. Outer cannula 34 serves to temporarily isolate implant 10 from the subcutaneous tissue and to dilate the subcutaneous canal initially created by tip 38.

Handle apparatus 44, well known to those of ordinary skill in the art, is adapted for use with the invention described herein but is not illustrated in detail. Tightening mechanism 46 enables handle 44 to grasp outer cannula 34 and thereby manipulate insertion tool 30.

In an example of operation, the physician manipulates handle 44, connected to the proximal end of outer cannula 34, thus pushing tip 38 through the dermis at the proximal end of the intended insertion area. The remainder of insertion tool 30 follows the path of tip 38 through the subcutaneous tissue until tip 38 protrudes through the distal end of the intended insertion area. Again, the instrument is designed for the surgeon to push the sharp point through the intact skin. However, an incision can be made initially if the surgeon so desires or when the size of the implant dictates.

Once insertion tool 30 and implant 10 are in the desired location, the physician pulls handle 44 to remove outer cannula 34 through the proximal end of the subcutaneous canal, thus exposing the subcutaneous tissue to implant 10. The physician then removes central shaft 32 from the subcutaneous canal by grasping tip 38 at textured surface 40, using a common forceps or other similar device, and pulling tip 38 and shaft 32 through the distal end of the canal, leaving implant 10 in the location and position desired, with the implant stabilized between the surgeon's thumb and index finger the tip and shaft are removed.

The second embodiment tool 30 can be made from materials such as stainless steel, rigid plastic, and/or carbon fibers. The handle 44 can be sterilizable while the remaining portion (central shaft 32, outer cannula 34, and tip 38) can be disposable and thus obviate the necessity for sterilization.

It is to be understood that while the invention has been described above in conjunction with preferred specific embodiments, the description and examples are intended to illustrate and not limit the scope of the invention, which is defined by the scope of the appended claims.

It is claimed:

1. A soft tissue tissue augmentation device comprising:

a longitudinally extending implant consisting essentially of a non-degradable, biocompatible material having a cavity longitudinally extending therein from at least one open cavity end thereof, the implant being dimensioned for subcutaneous placement under a glabellar facial wrinkle, a nasal labial fold, or under a lip, the material having pores of about 10 to about 50 microns therein, having textural compatibility with soft tissue, and being configured to maintain, when implanted, sufficient of the cavity for fibrous tissue ingrowth into the cavity through the open end thereof for anchoring of the implant thereby.

2. The soft tissue augmentation device as in claim 1 wherein the implant is flexible.

3. The soft tissue augmentation device as in claim 1 wherein the implant cavity longitudinally extends between open cavity ends, the implant being adapted to permit tissue ingrowth through both open ends thereof when implanted.

4. The soft tissue augmentation device as in claim 1 further comprising:

a releasable package for the implant, the package of sufficient construction to maintain the implant in a sterile condition when sterilely packaged therein and before release thereof.

5. The soft tissue augmentation device as in claim 1 or 4 further comprising:

an insertion tool by which the implant can be inserted into a selected soft tissue and the tool removed while leaving the implant in the selected tissue.

6. A soft tissue augmentation device comprising:

a plurality o longitudinally extending implants each consisting essentially of a non-degradable, biocompatible material having a cavity longitudinally extending therein from at least one open cavity end thereof, the implant being dimensioned for subcutaneous placement under a glabellar facial wrinkle, a nasal labial fold, or under a lip, the material having pores of about 10 to about 50 microns therein, having textural compatibility with soft tissue, and being configured to maintain, when implanted, sufficient of the cavity for fibrous tissue ingrowth into the cavity through the open end thereof for anchoring of the implant thereby, wherein one implant is different from another implant by at least one dimension, different dimensions of the one and the other implants being selected to correspond to at least two soft tissues selected for augmentation.

\* \* \* \* \*